United States Patent
Wilson

(10) Patent No.: US 11,733,197 B2
(45) Date of Patent: Aug. 22, 2023

(54) BIOSENSORS PRODUCED FROM ENZYMES WITH REDUCED SOLUBILITY AND METHODS OF PRODUCTION AND USE THEREOF

(71) Applicant: Siemens Healthcare Diagnostics Inc., Tarrytown, NY (US)

(72) Inventor: Michael S. Wilson, Waltham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 795 days.

(21) Appl. No.: 16/609,331

(22) PCT Filed: May 3, 2018

(86) PCT No.: PCT/US2018/030870
§ 371 (c)(1),
(2) Date: Oct. 29, 2019

(87) PCT Pub. No.: WO2018/204627
PCT Pub. Date: Nov. 8, 2018

(65) Prior Publication Data
US 2020/0064296 A1  Feb. 27, 2020

Related U.S. Application Data

(60) Provisional application No. 62/501,322, filed on May 4, 2017.

(51) Int. Cl.

| | | |
|---|---|---|
| *G01N 27/327* | (2006.01) | |
| *C12N 9/80* | (2006.01) | |
| *C12N 11/14* | (2006.01) | |
| *C12Q 1/00* | (2006.01) | |
| *C12Q 1/58* | (2006.01) | |
| *C12N 11/093* | (2020.01) | |
| *C12N 11/082* | (2020.01) | |
| *C12N 11/089* | (2020.01) | |

(52) U.S. Cl.
CPC .......... *G01N 27/3272* (2013.01); *C12N 9/80* (2013.01); *C12N 11/082* (2020.01); *C12N 11/089* (2020.01); *C12N 11/093* (2020.01); *C12N 11/14* (2013.01); *C12Q 1/003* (2013.01); *C12Q 1/58* (2013.01); *C12Y 305/01005* (2013.01)

(58) Field of Classification Search
CPC ... C12N 11/082; C12N 11/089; C12N 11/093; C12N 11/14; C12N 9/80; C12N 9/96; C12Q 1/003; C12Q 1/58; C12Y 305/01005; G01N 27/3272; G01N 27/333
See application file for complete search history.

(56) References Cited

U.S. PATENT DOCUMENTS

| | | | |
|---|---|---|---|
| 3,167,485 A * | 1/1965 | Katchalski | ........... C12N 11/089 530/409 |
| 4,476,005 A * | 10/1984 | Tokinaga | ............... C12Q 1/005 435/177 |
| 5,165,407 A | 11/1992 | Wilson et al. | |
| 5,556,760 A * | 9/1996 | Nakamura | ............... C12Q 1/58 257/253 |
| 6,051,389 A | 4/2000 | Ahl et al. | |
| 7,540,948 B2 | 6/2009 | Collier et al. | |
| 7,959,791 B2 | 6/2011 | Kjaer et al. | |
| 8,182,663 B2 * | 5/2012 | Collier | ................... C12Q 1/005 204/415 |
| 8,649,840 B2 * | 2/2014 | Sheppard, Jr. | ..... G01N 27/3272 600/345 |
| 2004/0256227 A1 | 12/2004 | Shin et al. | |
| 2006/0275857 A1 | 12/2006 | Kjaer et al. | |
| 2008/0302659 A1 | 12/2008 | Sheppard, Jr. et al. | |
| 2011/0286888 A1 | 11/2011 | Barlag | |
| 2013/0112558 A1 | 5/2013 | Collier et al. | |
| 2015/0082874 A1 | 3/2015 | Samproni et al. | |

FOREIGN PATENT DOCUMENTS

| | | |
|---|---|---|
| EP | 0247850 A1 | 12/1987 |
| JP | 2006514307 A | 4/2006 |
| JP | 2008502921 A | 1/2008 |
| JP | 2009031283 A | 2/2009 |
| JP | 2010519938 A | 6/2010 |
| JP | 2011226951 A | 11/2011 |
| JP | 5740754 B2 | 7/2015 |
| WO | 2015155665 A1 | 10/2015 |
| WO | 2018160644 A1 | 9/2018 |

OTHER PUBLICATIONS

International Search Report and Written Opinion of International Application No. PCT/US2018/0030870 dated Jul. 11, 2018.
European Search Report and Search Opinion of European Application No. 18794831.0 dated Apr. 6, 2020.
Butt et al., "Enzyme Urea Biosensor Based on a Modified Potentiometric PVC-Nonactin Membrane Electrode for Assay of Urea in Blood", Apr. 13, 1992, Analytical Letters, 25(9), pp. 1597-1615.
Sternberg et al., "Covalent enzyme coupling on cellulose acetate membranes for glucose sensor development";Dec. 15, 1988; Analytical Chemistry; vol. 60; No. 24; pp. 2781-2786.
Ang et al., "Development of an Amperometric-Based Glucose Biosensor to Measure the Glucose Content of Fruit"; Jan. 1, 2015; PLoS ONE 10(3); pp. 1-17.
Koncki et al., "Potentiometric determination of dialysate urea nitrogen", 2000, Talanta, 52, pp. 13-17.

* cited by examiner

*Primary Examiner* — Blaine Lankford

(57) ABSTRACT

Multi-use biosensors are disclosed that include enzymes that have been modified to reduce the solubility thereof; the multi-use biosensors are used to detect analytes in fluidic biological samples, and the biosensors also maintain their enzyme activity after many uses. Multi-sensor arrays are disclosed that include multiple biosensors. Also disclosed are methods of producing and using these devices.

23 Claims, 4 Drawing Sheets

BIOSENSORS PRODUCED FROM ENZYMES WITH REDUCED SOLUBILITY AND METHODS OF PRODUCTION AND USE THEREOF

CROSS REFERENCE TO RELATED APPLICATIONS/INCORPORATION BY REFERENCE STATEMENT

The subject application claims benefit under 35 USC § 119(e) of U.S. provisional Application No. 62/501,322, filed May 4, 2017. The entire contents of the above-referenced patent application are hereby expressly incorporated herein by reference.

STATEMENT REGARDING FEDERALLY SPONSORED RESEARCH OR DEVELOPMENT

Not Applicable.

BACKGROUND

A sensor, also called a detector, is a device that measures a physical quantity and converts it to a signal which may be read by an observer or by an instrument. Sensors are used in chemical and biochemical testing to determine characteristics of an analyte of interest within a specimen or sample. In biomedicine and biotechnology, sensors which detect analytes having a biological component, such as cells, protein, or nucleic acid, are referred to as biosensors.

Biosensor arrays, in which multiple biosensors are grouped into a single unit, are useful in chemistry and medicine to determine the presence and/or concentration of a biological analyte. For example, various types of analytical tests related to patient diagnosis and therapy can be performed by analysis of a liquid sample taken from a patient. Bodily fluids commonly tested include urine, blood, plasma, saliva, cerebrospinal fluid, pleural fluid, and the like. Blood samples, for example, are routinely analyzed to obtain measurements of the partial pressures of $CO_2$ and $O_2$ and concentrations of electrolytes and metabolites in the blood. To determine the presence and concentrations of biological analytes, biosensors are generally used which include immobilized enzymes to attract and capture the analytes. Specifically, potentiometric biosensors are often employed which can utilize an ion-selective electrode or an electrode having an ion-permeable membrane that selectively permits the ion of interest to diffuse through. The operating principle is based on the measureable potential difference that is created when an ion equilibrates between two phases.

A number of different analyzers currently exist for making such measurements utilizing rigid layered sensor assemblies and electrical circuits. Such sensor assemblies are used to assess the condition of medical patients through primary clinical indications. Because of the frequency with which many patients are tested, the ability to use small sample sizes for performing analysis is desirable. Patients in intensive care units may require a sampling frequency of 15-20 per day for blood gas and clinical chemistry measurements. In these cases, analyzing small blood samples is desirable, due to the relatively large number of samples taken in a relatively short period of time. Further, to limit the number of tests performed, it is desirable to gather as much information as possible with each test.

Currently, single-use biosensors and multi-use biosensors are available for use in sensor arrays, such as the sensor arrays set forth in U.S. Publication Nos. 2015/0082874 and 2011/0286888 and International Publication No. WO 2015/155665 (the entire contents of each of which are hereby expressly incorporated herein by reference). One example of an assay amenable to biosensor measurement is the Blood Urea Nitrogen (BUN) assay. The BUN assay measures the amount of nitrogen in blood from the waste product, urea. Urea is a by-product produced by the kidneys when protein is broken down. While urea is produced in the liver, it passes through the kidneys, and measuring BUN allows medical and clinical practitioners to assess the renal function of patients. Higher than normal BUN levels indicate that a patient's kidneys are not functioning properly. Single-use BUN biosensors are currently available; said biosensors use a range of urease immobilization methods such as glutaraldehyde cross-linking (see, for example, the currently available iSTAT™ test cartridges available from Abbott Point of Care Inc., Princeton, N.J.). In general, urease is deposited on the electrode and "held in place" by cross-linking into an insoluble form for entrapment in a polymer. A cover membrane is then typically applied to further retain the enzyme and provide protection from fouling, interferents, etc. However, problems have been encountered when attempting to adapt this technology to produce a multi-use BUN biosensor. A poor use-life has typically been observed for multi-use BUN biosensors; the poor use-life is the result of various factors that include (but are not limited to) an insufficient amount of active urease often being immobilized on the biosensor, performance degradation due to loss of urease from leeching over time, and use-based enzyme degradation.

DETAILED DESCRIPTION

Figure 1:
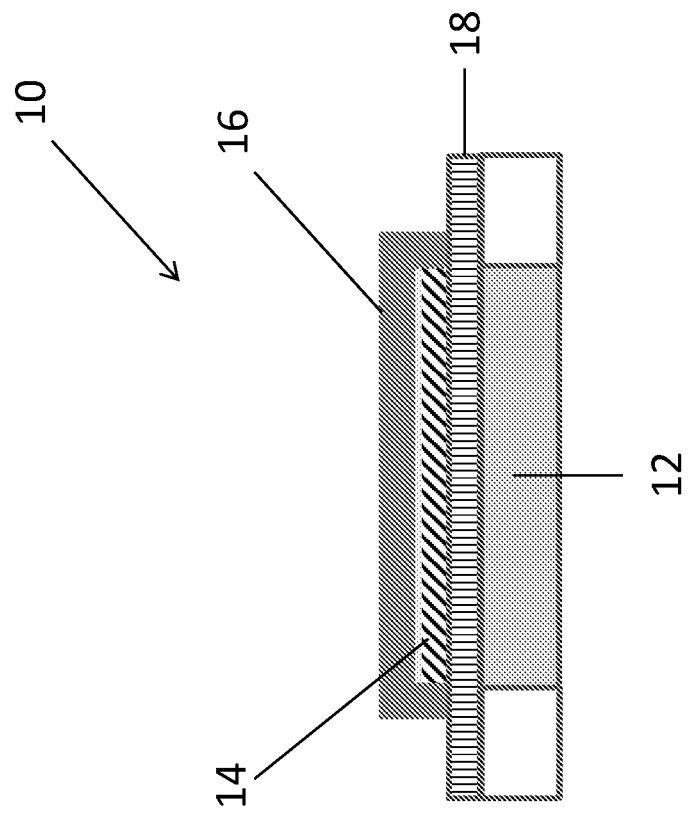
FIG. 1 is a perspective view of a multi-use biosensor constructed in accordance with the presently disclosed inventive concept(s).

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, and/or methods disclosed herein can be made and executed without undue experimentation in light of the present disclosure. While the articles, compositions, and methods of the inventive concept(s) have been described in terms of particular embodiments, it will be apparent to those of skill in the art that variations may be applied to the articles, compositions and/or methods and in the steps or in the sequence of steps of the methods described herein without departing from the concept, spirit, and scope of the inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second,"

"third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The term "sample" as used herein will be understood to include any type of biological sample that may be utilized in accordance with the presently disclosed inventive concept(s). Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "purified" as used herein means at least one order of magnitude of purification is achieved compared to the starting material or of the natural material, for example but not by way of limitation, two, three, four, or five orders of magnitude of purification of the starting material or of the natural material. Thus, the term "purified" as utilized herein does not necessarily mean that the material is 100% purified, and therefore such term does not exclude the presence of other material(s) present in the purified composition.

The term "electrode" as used herein refers to any type of conductor or medium that is capable of functioning in accordance with the presently disclosed inventive concept(s). Non-limiting examples of electrodes that fall within the scope of the presently disclosed inventive concept(s) include electrochemical cells comprising a plurality of electrodes. Exemplary electrochemical cell constructs include a two-electrode cell comprising one indicator electrode and one reference electrode, a two-electrode cell comprising one anode and one cathode, a three-electrode cell comprising one anode, one cathode and one reference electrode, and a four-electrode cell comprising two working electrodes, one counter electrode, and one reference electrode.

Currently, multi-use biosensors are available for use in sensor arrays. However, these biosensors typically have a short use-life, generally due to insufficient active enzyme immobilized on the biosensor, degraded performance caused by the loss of the enzyme leeching over time, degradation of the enzyme simply due to use, and/or insufficient enzyme activity due to fouling and/or interferents.

Therefore, there is a need in the art for new and improved multi-use biosensors which solve the problems of the current multi-use biosensors of the prior art while also being able to be used in a sensor array assembly. In particular, there is a need in the art for multi-use biosensors (such as BUN and other enzyme-based biosensors) that possess at least a 14-day use-life (such as, but not limited to, at least a 20-, 21-, 22-, 23-, 24-, 25-, 26-, 27-, 28-, 29-, or 30-day use-life) and at least a 1000 sample capability (such as, but not limited to, at least a 1500, 2000, 2500, or 3000 sample capability), while substantially maintaining the integrity, response, and precision of the biosensor.

Turning now to the Drawings (and in particular FIG. 1), certain embodiments of the presently disclosed inventive concept(s) are directed to a multi-use biosensor 10 for detecting the presence and/or concentration of at least one target analyte in a fluidic biological sample. The multi-use biosensor 10 comprises an electrode 12 with a modified enzyme 14 dispensed on at least a portion thereof, and a membrane 16 disposed on at least a portion of the modified enzyme 14. The membrane 16 (also referred to herein interchangeably as a "cover membrane") functions to immobilize the modified enzyme 14 on the electrode 12. The enzyme 14 has been modified to reduce the solubility thereof through reaction of at least one functional group thereon with a reactant such that the modified enzyme 14 is substantially insoluble in the fluidic biological sample and in calibration reagents utilized with the multi-use biosensor 10. For example (but not by way of limitation), the modified enzyme 14 may be substantially insoluble in the fluidic biological sample and the calibration reagents used with the multi-use biosensor 10 but substantially soluble in a buffer that has a lower ionic strength than the fluidic biological sample and the calibration reagents. In addition, following modification, the enzyme 14 still retains an active site that is capable of interaction with the at least one target analyte so that the at least one target analyte can be detected through said interaction (and capture by the modified enzyme 14).

In a particular (but non-limiting) embodiment, the multi-use biosensor 10 is further defined as a multi-use blood urea nitrogen (BUN) biosensor. In this embodiment, the modified enzyme 14 present in the biosensor 10 is a modified urease. In a particular (but non-limiting) example, the urease has been modified by interaction with a long chain biotin.

The multi-use biosensor 10 of the presently disclosed inventive concept(s) overcomes the defects and disadvantages of the prior art by reducing the solubility of the enzyme 14 to prevent leeching of the enzyme 14 from the biosensor 10 and thereby maintain integrity of the biosensor 10, thus providing the multi-use biosensor 10 with an increased use-life and sample capability. For example (but not by way of limitation), the multi-use biosensor 10 may substantially maintain the integrity thereof over a use-life of at least about 14 days and a sample capability of at least about 3000 samples.

Currently there are two general approaches utilized to produce multi-biosensor array products. In these approaches, the individual sensors are produced separately and then stitched together in an array after the chemistry has been performed on each sensor; alternatively, a single substrate is used that contains multiple electrodes in an array, and the appropriate coupling chemistry (e.g. enzyme attachment by cross-linking) is performed on each electrode (typically by dispensing reagents sequentially). This second option possesses the benefits of reduced cost and reduced sample volume; however, there is an increased risk that the whole array will be ruined if any issues arise in any one of the electrode chemistries during manufacturing.

Therefore, one of the defects of the standard cross-linking methods of the prior art is that the coupling chemistry is performed directly on the electrode during manufacture, and this direct interaction increases the risk and complexity of the manufacture, especially if there are multiple electrodes on which one or more coupling chemistries are performed in a "single substrate" multi-sensor array product. The presently disclosed inventive concept(s) overcomes this defect by performing the key enzyme chemistry external to the final array manufacturing process, thereby significantly reducing the risks associated with the manufacturing process. By significantly reducing the solubility of the enzyme in the sample and test matrix, while being able to dispense the enzyme from another matrix in which it is freely soluble, the modified enzyme can be validated (such as for activity, kinetics, etc.) before attachment to the electrode during manufacture, thereby removing the need to cross-link the enzyme onboard the array.

Turning back to the particular components of the multi-use biosensor 10, any type of sensor known in the art as capable of use in a biosensor comprising an enzyme can be utilized in accordance with the presently disclosed inventive concept(s). For example (but not by way of limitation), the biosensor 14 may be a potentiometric, amperometric, impedimetric, or conductometric sensor. In addition, any electrodes known in the art as capable of use with one of the above types of biosensors can be utilized as the electrode 12 in accordance with the presently disclosed inventive concept(s). Non-limiting examples of electrodes 12 that may be utilized include ion-specific or ion-selective electrodes (ISE). The specific type of electrode selected will be dependent on the sensor type (i.e., potentiometric, amperometric, impedimetric, conductometric, etc.). In certain non-limiting embodiments, the electrode 12 may contain a sensing layer 18. Any sensing layers that may be utilized with an electrode 12 and that known in the art or otherwise contemplatable by a person of ordinary skill in the art may be utilized in accordance with the presently disclosed inventive concept(s). One non-limiting example of a sensing layer 18 that falls within the scope of the presently disclosed inventive concept(s) is a $NH_4^+$ sensing layer.

The electrode 12 may possess any shape that allows the electrode to function in accordance with the presently disclosed inventive concept(s). For example, in certain non-limiting embodiments, the electrode 12 may be planar or circular in shape. The electrode 12 can be fabricated by any method known in the art or otherwise contemplated herein. Examples of fabrication methods that can be utilized in accordance with the presently disclosed inventive concept(s) include, but are not limited to, screen printing, metal sputtering, photolithography, or any other standard electrode manufacturing method.

The target analyte(s) may be any analyte present in a fluidic biological sample and that is known in the art or otherwise contemplated herein as being detectable by an enzyme-containing biosensor. Non-limiting examples of target analytes detectable by the multi-use biosensors of the presently disclosed inventive concept(s) include blood urea nitrogen (BUN), glucose, glutamate, lactate, ethanol, ascorbic acid, choline acetylcholine, creatinine, cholesterol, pyruvate, bilirubin, and the like.

Any enzyme known in the art as capable of use in a biosensor for detection of a target analyte in a fluidic biological sample may be utilized as the enzyme 14 in accordance with the scope of the presently disclosed inventive concept(s). Non-limiting examples of enzymes useful in the multi-use biosensors 10 include urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, pyruvate dehydrogenase, combinations thereof, and the like.

The at least one modified functional group present on the enzyme 14 may be any functional group known in the art that is capable of modification via reaction with a reactant. Examples of functional groups include, but are not limited to, an aldehyde-, amine-, carbonyl-, carboxyl-, hydroxyl-, ketone-, maleimide-, sulfhydryl-, and thiol-reactive groups.

Any reactants known in the art or otherwise contemplated herein that are capable of interacting with a functional group on an enzyme in the manner described herein can be utilized within the scope of the presently disclosed inventive concept(s). One non-limiting example of a functional group-reactant interaction includes an interaction between amine groups on an enzyme with a long chain biotin. Another non-limiting example of a functional group-reactant interaction includes interaction between COOH functional groups on an enzyme with 1-ethyl-3-(-3-dimethylaminopropyl) carbodiimide hydrochloride ("EDC")/N-hydroxysuccinimide esters ("NHS"). However, any functional group-reactant interactions (as well as any combination of multiple functional group-reactant interactions) may be utilized in accordance with the presently disclosed inventive concept(s) so long as said interaction(s) has an effect on the solubility of the enzyme 14 and does not substantially affect the active site and/or activity of the enzyme 14.

The modification to the enzyme can be detected by any method known or otherwise contemplatable in the art. For example (but not by way of limitation), the reactant attached to the enzyme may increase the molecular weight and/or change the isoelectric point of the modified enzyme when compared to the molecular weight and/or isoelectric point of unmodified enzyme.

The modified enzyme 14 may be present on the electrode 12 at any percentage of surface area that allows the biosensor 10 to perform in accordance with the presently disclosed inventive concept(s). For example (but not by way of limitation), the modified enzyme 14 must be present on a sufficient amount of surface area of the electrode 14 to allow for sufficient capture of the target analyte by the biosensor 10. In certain particular (but non-limiting) embodiments, the modified enzyme 14 may be present on the electrode 12 at a percent surface area of about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, about 100%, about 101%, about 102%, about 103%, about 104%, about 105%, about 110%, about 115%, about 120%, and above. Stated another way, the modified enzyme 14 may have a surface area of less than, equal to, or greater than the surface area of electrode 12. In addition, the scope of the presently disclosed inventive concept(s) also includes the presence of the modified enzyme 14 on the electrode 12 at any percent surface area that falls within any range formed from the combination of two values listed above (for example, a range of from about 10% to about 120%, a range of from about 20% to about 105%, a range of from about 30% to about 100%, a range of from about 40% to about 75%, etc.).

In certain non-limiting embodiments, there is no physical attachment between the modified enzyme 14 and the electrode 12. Instead, the cover membrane 16 is placed over the modified enzyme 14 to hold the modified enzyme 14 in place on the electrode 12. Cover membranes have previously been used as components of biosensors; non-limiting examples thereof that may be utilized as the membrane 16 in accordance with the presently disclosed inventive concept(s) are disclosed in U.S. Pat. No. 7,959,791 (the entire contents of which are hereby expressly incorporated herein by reference). Therefore, a person of ordinary skill in the art would be aware of cover membranes that can be utilized in accordance with the presently disclosed inventive concept(s).

In certain embodiments, the cover membrane 16 is permeable to the target analyte to be detected but substantially impermeable to the modified enzyme 14. For example (but not by way of limitation), the membrane 16 can be semipermeable in order to allow passage of the biological analytes therethrough and removal of any by-product from the sensor 10. In addition, the membrane 16 may be formed of any material known in the art or otherwise contemplated herein that allows the biosensor 10 to function in accordance with the presently disclosed inventive concept(s). That is, the membrane 16 must be formed of a material that is permeable to the target analyte(s) to be detected but is substantially impermeable to the modified enzyme 15. Non-limiting examples of materials from which the membrane 16 can be formed include polyurethane, silicone, poly(vinyl chloride), combinations thereof, and the like. One particular (but non-limiting) example of a material from which the membrane can be constructed is HydroMed™ D7, a polyester based polyurethane (AdvanSource Biomaterials Corp., Wilmington, Mass.).

The membrane 16 can be easily washed with a wash solution in between uses to remove any by-product. Prior to the use of a modified enzyme with reduced solubility (and which is not cross-linked to the electrode) in the presently disclosed inventive concept(s), the dense cross-linked enzyme layer could retain the by-products and cause carryover from earlier biological samples.

The modification of the enzyme to significantly reduce the solubility thereof provides surprising and unexpected improvements over the prior art methods of covalently coupling the enzyme directly to the biosensor. The use of modified enzyme in accordance with the presently disclosed inventive concept(s) provides performance benefits that are (1) better than the use of non-cross-linked, unmodified enzyme, and (2) similar to the use of conventional on-board cross-linked enzyme (but without requiring the use of cross-linking); as such, these performance benefits lead to a longer use-life for the biosensor while also maximizing the biosensor's response (and therefore also the precision of the biosensor). Also, a wide variety of well-known chemistries can be utilized to reduce the solubility of the enzyme through reaction of its functional groups, and these various chemistries can be performed offline relative to the electrode dispensing and assembly of any biosensor arrays; in addition, the use of these chemistries enables critical enzyme modifications to be performed offline during biosensor array manufacturing and thus leads to a longer use-life for the biosensor and also maximizes the response and precision of the biosensor. The modified enzyme can be prepared and validated before any dispensing begins, thereby reducing the chance of a "bad" biosensor being created (i.e., by immobilizing an insufficient amount of active enzyme on the electrode) and thereby ruining the production of an entire biosensor array assembly. Good enzyme stability is also achieved by using the appropriate reactants for reducing the solubility of the enzyme.

The presently disclosed inventive concept(s) eliminates the need to replace the biosensors after each use, or after several uses. Rather, the biosensors of the presently disclosed inventive concept(s) have an enhanced use-life, and can simply be washed with wash solution between uses. Moreover, the presently disclosed inventive concept(s) reduces carryover between biological samples, because the lack of cross-linking of enzyme to electrode reduces entrapment in the cross-linked matrix and allows for a better cleaning between biological sample runs. As such, the presently disclosed inventive concept(s) improves the prior art by reducing the amount of turnaround time (because multiple tests can be conducted at once) and reducing the amount of maintenance time spent on the instrumentation, such as blood gas analyzers.

Figure 2:
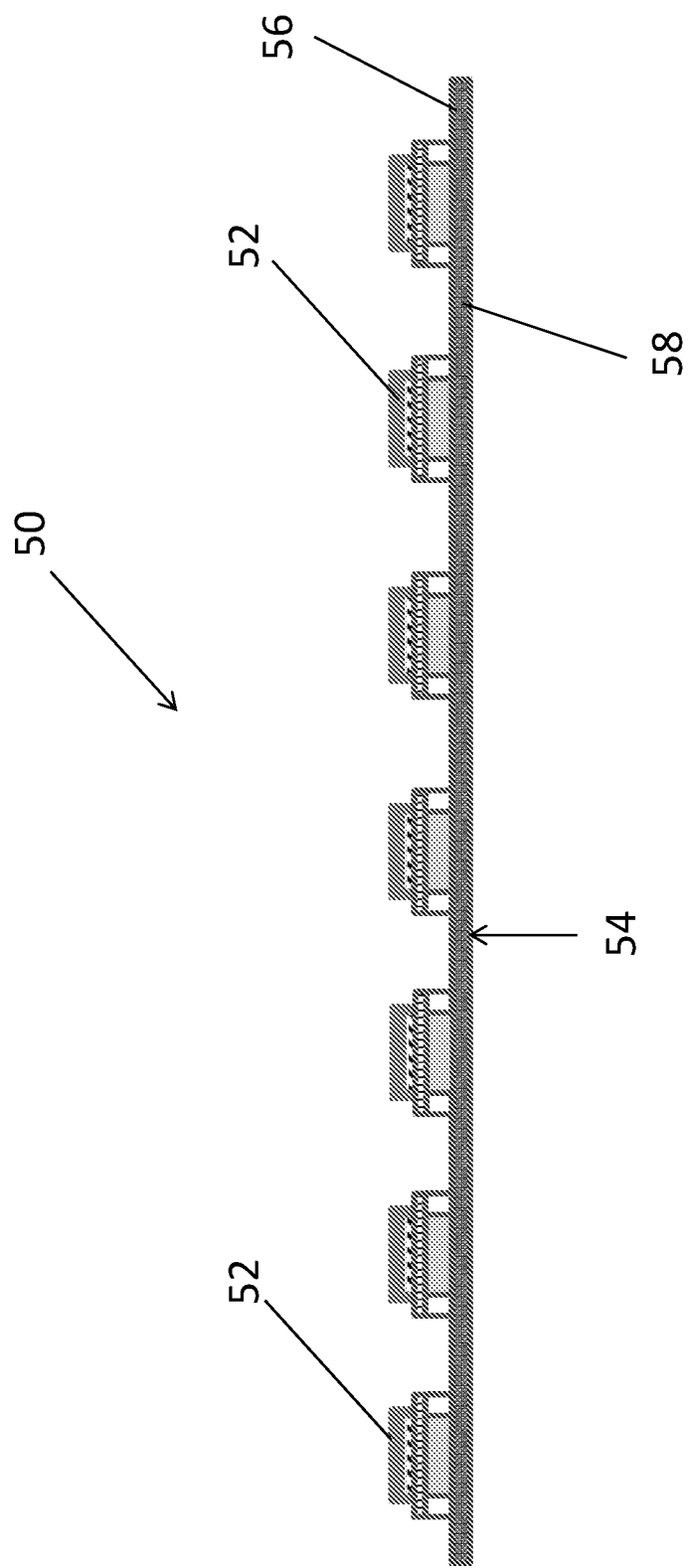
FIG. 2 is a perspective view of a multi-use biosensor array assembly constructed in accordance with the presently disclosed inventive concept(s).

As shown in FIG. 2, certain embodiments of the presently disclosed inventive concept(s) are directed to a multi-use biosensor array assembly 50 that includes a plurality of multi-use biosensors (two of which are indicated in FIG. 2 by the general reference numeral 52) in combination with a substrate 54, wherein at least one of the multi-use biosensors 52 is any of the biosensors 10 comprising modified enzyme 14 having reduced solubility, as described in detail herein above or otherwise contemplated herein. The substrate 54 has a first surface 56 and a second surface 58 opposite the first surface 56, and each of the plurality of multi-use biosensors 52 are spatially positioned on at least one of the first and second surfaces 56 and 58 of the substrate 54.

When at least two of the multi-use biosensors 52 are multi-use biosensors 10 comprising modified enzymes 14 with reduced solubility, the enzymes 14 present in the two multi-use biosensors 10 may be the same or different from one another. In certain embodiments, all of the enzymes of the biosensors 52 present in the array assembly 50 may be different; alternatively, at least two enzymes of each of the plurality of multi-use biosensors 52 present in the multi-use biosensor array assembly 50 may be the same.

The multi-use biosensors 10 of the presently disclosed inventive concept(s) may be produced by any methods known in the art or otherwise contemplatable by a person having ordinary skill in the art. Certain additional embodiments of the presently disclosed inventive concept(s) are directed to a method of producing any of the multi-use analyte biosensors described herein above or otherwise contemplated herein, wherein the biosensor can be prepared and manufactured to provide a stable and qualified product. In the method, an enzyme present in a first buffer is modified by reacting at least one functional group on the enzyme with a reactant, thereby producing a modified enzyme that has a reduced solubility when compared to unmodified enzyme; the resultant modified enzyme is substantially insoluble in the fluidic biological sample and in calibration reagents utilized with the multi-use biosensor, and the modified enzyme still retains an active site that is capable of interacting with the target analyte for detection of the target analyte. A precipitate of the modified enzyme is then formed, and the precipitate of modified enzyme is re-dissolved in a second buffer to provide a modified enzyme solution; the second buffer has a lower ionic strength than the first buffer, whereby the modified enzyme is substantially soluble in the second buffer but less soluble or substantially insoluble in the first buffer. A specific amount of the modified enzyme solution is dispensed on at least a portion of an electrode and dried thereon. A membrane is then disposed on at least a portion of the modified enzyme and electrode, and the membrane immobilizes the modified enzyme on the electrode.

The method may also include one or more optional steps, such as (but not limited to): (i) purifying the enzyme away from excipients by buffer exchange into the first buffer prior to modification of the enzyme; and/or (ii) qualifying an activity of the enzyme before and/or after deposition on the electrode. For example, once the enzyme is modified and prior to deposition on the electrode, testing can be conducted to determine enzyme activity. Then, upon qualification thereof, a desired amount of modified enzyme can be dispensed onto the electrode and immobilized thereon via the membrane.

The multi-use biosensor array assemblies 50 of the presently disclosed inventive concept(s) may be produced by any methods known in the art or otherwise contemplatable by a person having ordinary skill in the art. Further embodiments of the presently disclosed inventive concept(s) are directed to a method of producing a multi-use biosensor array assembly. In the method, a plurality of multi-use biosensors are formed and spatially disposed on at least one surface of a substrate. At least one of the plurality of multi-use biosensors so formed is any of the multi-use biosensors comprising modified enzyme having reduced solubility, as described in detail herein above or otherwise contemplated herein; the multi-use biosensor comprising modified enzyme may also be formed by any of the methods described in detail herein above or otherwise contemplated herein.

Yet further embodiments of the presently disclosed inventive concept(s) are directed to a method for detecting the presence and/or concentration of a target analyte in a fluidic biological sample. In the method, a fluidic biological sample is inserted into a blood gas, electrolyte, and/or metabolite instrument containing any of the multi-use biosensors described in detail herein above. The method then includes measuring the presence and/or concentration of the target analyte captured by the multi-use biosensor and the reporting of same by the instrument. For example (but not by way of limitation), target analyte ions disperse though the multi-use biosensor and bind to the corresponding enzyme present on the multi-use biosensor. At that time, the ion level can be measured by any of the various methods currently known in the art or otherwise contemplated herein (including, but not limited to, change in membrane potential or amperometry).

In addition, other embodiments of the presently disclosed inventive concept(s) are directed to a method for detecting the presence and/or concentration of a plurality of target analytes in a fluidic biological sample. In the method, a fluidic biological sample is inserted into a blood gas, electrolyte, and/or metabolite instrument containing any of the multi-use biosensor array assemblies described in detail herein above. The method then includes measuring the presence and/or concentration of each of a plurality of target analytes captured by the individual multi-use biosensors of the array assembly and the reporting of same by the instrument. Therefore, the presently disclosed inventive concept(s) envisions simultaneously obtaining measurements for multiple analytes from multiple multi-use biosensors.

In each of the above detection methods, the fluidic biological sample may be selected from the group comprising whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

EXAMPLES

An Example is provided hereinbelow. However, the presently disclosed inventive concept(s) is to be understood to not be limited in its application to the specific experimentation, results and laboratory procedures. Rather, the Examples are simply provided as one of various embodiments and are meant to be exemplary, not exhaustive.

The following Example is directed to the production and use of a BUN multi-use biosensor produced using urease that has been modified to reduce the solubility thereof.

1. Urease (474 mg, BBI Solutions, Cardiff, UK), was dissolved in 100 mM Phosphate Buffered Saline (PBS, 0.936 ml), and the excipients were removed using a 7K MWCO ZEBA™ Column (Thermo Fisher Scientific Inc., Waltham, Mass.). The final volume of the urease solution was adjusted to 1.26 ml using PBS.

Purification of urease from excipients as in the above step proved useful, since the excipients reduce the effectiveness of the reaction. However, this step is not required; alternatively, high concentrations of reactants could be utilized in the presence of excipient.

2. The urease was then reacted with at least 30-molar equivalents of Sulfo-NHS-LC-LC-Biotin (160 μl of 125 mg/ml in water; Thermo Fisher Scientific Inc., Waltham, Mass.) via gentle mixing for 2 hours.

3. A precipitate, which contained the insoluble biotinylated urease, was then formed and collected by centrifuge.

4. The supernatant was decanted, and the modified urease was then re-dissolved in 10 mM PBS (2 ml). This PBS buffer has a lower ionic strength than the 100 mM PBS used in the purification reaction of step 1.

Optionally, the excess reagents can be removed using a second ZEBA™ Column buffer exchange (10 mM PBS).

While not wishing to be bound to a particular theory, it is possible that the mechanism here likely involves the well-known "salting out" mechanism. A key point in this step is that the modified enzyme is soluble in lower ionic strength buffer/water but less soluble/insoluble in higher strength buffers, such as calibrator solutions and patient samples (typically >130 mM).

5. The activity of the modified enzyme was measured using a standard optical urease assay. Typically, some loss in activity might be observed at this point; however, the level of loss is minimal and still provides for sufficient enzyme activity for the biosensor.

6. If desired, the enzyme could be lyophilized into vials for long-term storage at this point.

7. The biotinylated urease solution was adjusted to the desired activity/dispensing concentration (e.g. 26 KU/ml), dispensed onto a screen-printed Ag/AgCl electrode (1.5 mm×0.5 mm) that contained a nonactin-based $NH_4^+$-sensing layer, and allowed to dry (e.g. Butt and Cammann (1992) *Anal. Lett.*, 25:1597). This step utilized a 27 gauge needle for 0.01 s, and 1.4 psi dispensing parameters. This dispensing step was repeated twice more, with 15 minutes between each dispensing step.

Following drying, a cover membrane was added by dispensing a layer of HydroMed™ D7 urethane (4% in THF/cyclohexanone (9:1), 0.01 s, 3.6 psi; AdvanSource Biomaterials Corp., Wilmington, Mass.)) on top of the enzyme.

Following step (7), sensor fabrication was complete.

Figure 3:
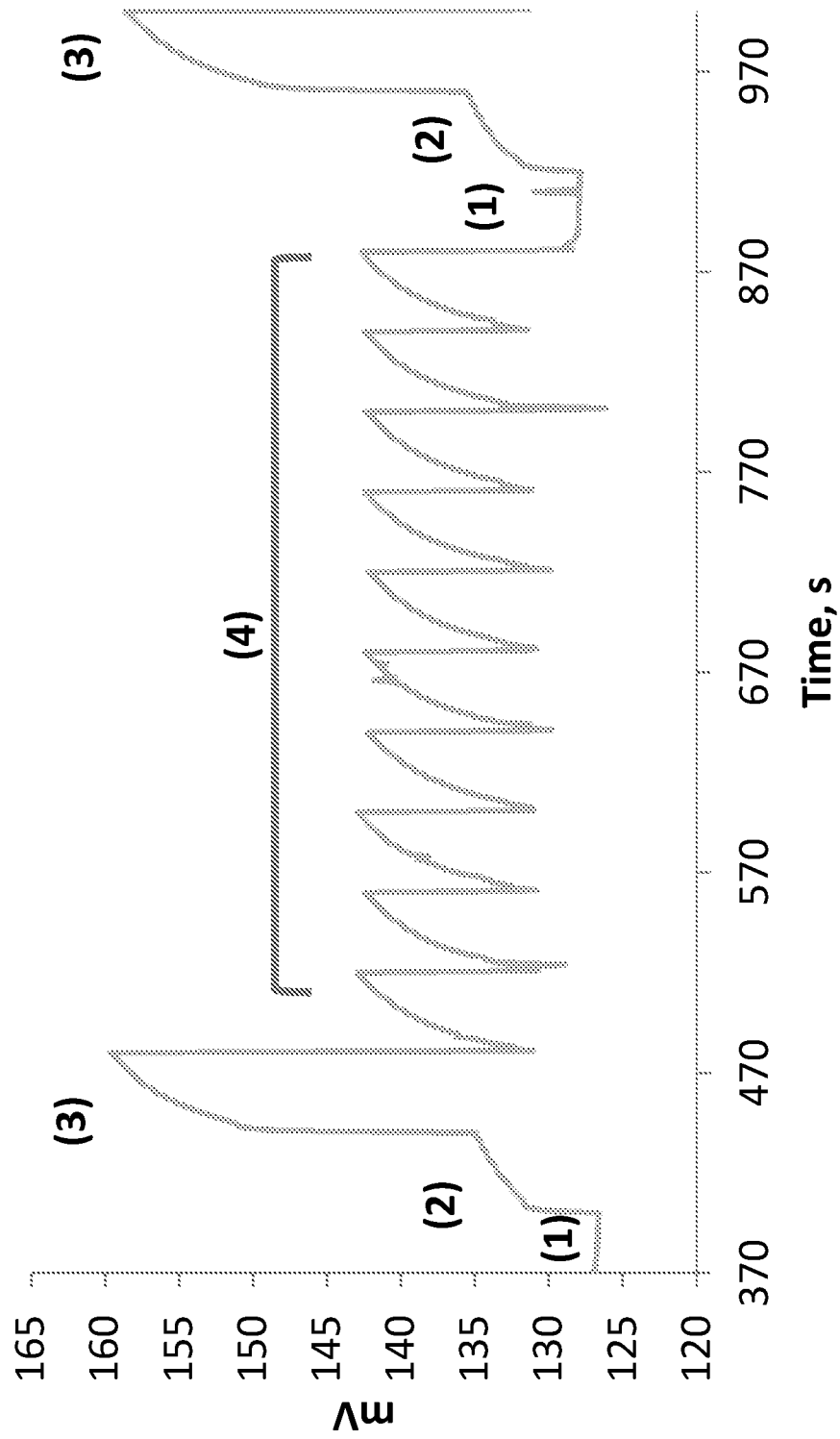
FIG. 3 is a graphical representation of the assay response kinetics of the multi-use biosensor constructed in accordance with the presently disclosed inventive concept(s) upon exposure to 0, 5, and 27 mg/dL BUN calibrator solutions (1, 2, and 3) and repeated blood samples (4).
Figure 4:
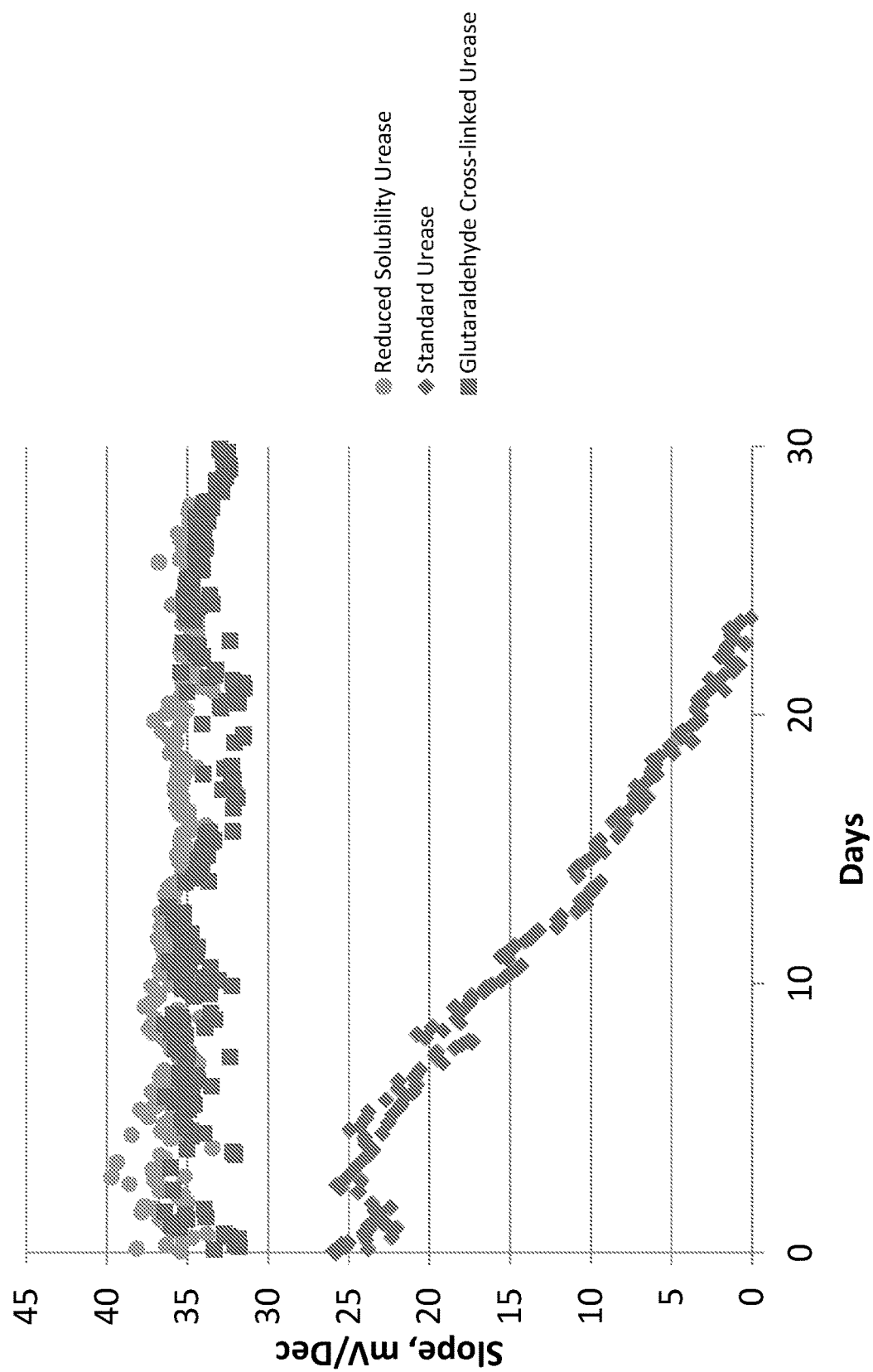
FIG. 4 is a graphical representation of the potentiometric BUN (blood urea nitrogen) sensor dose-response slopes over 30 days in 5 and 27 mg/dL BUN Calibrator solution at 37° C. (62 calibrator and 10 blood samples per day) of the multi-use biosensor constructed in accordance with the presently disclosed inventive concept(s) (○) compared to a conventional multi-use biosensor containing non-cross-linked urease (◇) as well as a conventional multi-use biosensor containing cross-linked urease (□).

The improved performance of the BUN sensor (containing modified urease having reduced solubility) relative to free standard enzyme is shown in FIGS. 3 and 4. FIGS. 3 and 4 demonstrate the assay response kinetics and dose-response slope of the sensor, respectively, to 5 mg/dL and 27 mg/dL BUN calibrator solutions, as well as blood samples. The sensors typically maintained full stability for at least two weeks, and up to 30 days.

Non-Limiting Embodiments of the Inventive Concept(S)

Certain embodiments are directed to a multi-use biosensor for detecting the presence and/or concentration of at least one target analyte in a fluidic biological sample. The multi-use biosensor comprises an electrode, a modified enzyme, and a membrane. The modified enzyme is dispensed on at least a portion of the electrode; the enzyme has been modified to reduce the solubility thereof through reaction of at least one functional group thereon with a reactant such that the modified enzyme is substantially insoluble in the fluidic biological sample and in calibration reagents utilized with the multi-use biosensor, and wherein the modified enzyme comprises an active site that interacts with the target analyte for detection of the target analyte. The membrane is disposed on at least a portion of the modified enzyme, wherein the membrane immobilizes the modified enzyme on the electrode.

In certain embodiments, the multi-use biosensor may be further defined as a potentiometric analyte biosensor.

In certain embodiments, the at least one functional group on the modified enzyme is selected from the group comprising an aldehyde-, amine-, carbonyl-, carboxyl-, hydroxyl-, ketone-, maleimide-, sulfhydryl-, and thiol-reactive group.

In certain embodiments, the reactant comprises a long chain biotin.

In certain embodiments, the membrane is permeable to the target analyte to be detected but substantially impermeable to the modified enzyme.

In certain embodiments, the membrane is formed of a material selected from the group comprising polyurethane, silicone, poly(vinyl chloride), and combinations thereof.

In certain embodiments, the enzyme is selected from the group comprising urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, and pyruvate dehydrogenase.

In certain embodiments, the multi-use biosensor is further defined as a multi-use blood urea nitrogen (BUN) biosensor, and the at least one modified enzyme is a modified urease.

In certain embodiments, the biosensor has at least a 14 day use-life.

In certain embodiments, the modified enzyme is substantially soluble in a buffer that has a lower ionic strength than the fluidic biological sample and the calibration reagents used with the multi-use biosensor.

In certain embodiments, the reactant attached to the enzyme increases the molecular weight and/or changes the isoelectric point of the modified enzyme when compared to the molecular weight and/or isoelectric point of unmodified enzyme.

Certain embodiments are directed to a multi-use biosensor array assembly, comprising a substrate and a plurality of multi-use biosensors. Each of the plurality of multi-use biosensors are spatially positioned on at least one surface of the substrate, and at least one of the plurality of multi-use biosensors is any of the multi-use biosensors described immediately herein above.

Certain embodiments are directed to a method of producing a multi-use biosensor, the method comprising the steps of: (a) modifying an enzyme present in a first buffer by reacting at least one functional group on the enzyme with a reactant, thereby producing a modified enzyme that has a reduced solubility when compared to unmodified enzyme such that the modified enzyme is substantially insoluble in the fluidic biological sample and in calibration reagents utilized with the multi-use biosensor, and wherein the modified enzyme comprises an active site that interacts with the target analyte for detection of the target analyte; (b) forming a precipitate of modified enzyme; (c) redissolving the precipitate of modified enzyme in a second buffer to provide a modified enzyme solution, wherein the second buffer has a lower ionic strength than the first buffer, whereby the modified enzyme is substantially soluble in the second buffer but less soluble or substantially insoluble in the first buffer; (d) dispensing a specific amount of the modified enzyme solution on at least a portion of an electrode; (e) drying the modified enzyme solution on the electrode; and (f) disposing a membrane on at least a portion of the modified enzyme and electrode, wherein the membrane immobilizes the modified enzyme on the electrode.

In certain embodiments, the multi-use analyte biosensor is further defined as a potentiometric analyte biosensor.

In certain embodiments: (i) the at least one functional group on the enzyme is selected from the group comprising an aldehyde-, amine-, carbonyl-, carboxyl-, hydroxyl-, ketone-, maleimide-, sulfhydryl-, and thiol-reactive group; (ii) the reactant comprises a long chain biotin; (iii) the membrane is permeable to the target analyte to be detected but substantially impermeable to the modified enzyme; (iv) the membrane is formed of a material selected from the group comprising polyurethane, silicone, poly(vinyl chloride), and combinations thereof; (v) the enzyme is selected from the group comprising urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, and pyruvate dehydrogenase; and/or (vi) the reactant attached to the enzyme increases the molecular weight and/or changes the isoelectric point of the modified enzyme when compared to the molecular weight and/or isoelectric point of unmodified enzyme.

In certain embodiments, the multi-use biosensor is further defined as a multi-use blood urea nitrogen (BUN) biosensor, and the at least one modified enzyme is urease.

In certain embodiments, the biosensor so produced has at least a 14 day use-life.

In certain embodiments, step (a) of the method described above reduces the solubility of the modified enzyme to a level whereby the modified enzyme is substantially insoluble in the fluidic biological sample and in calibration reagents utilized with the multi-use biosensor but is substantially soluble in a buffer that has a lower ionic strength than the fluidic biological sample and the calibration reagents.

In certain embodiments, the method described above further comprises at least one of the steps of: (g) purifying the enzyme from excipients by buffer exchange into the first buffer prior to step (a); and (h) measuring an activity of the enzyme prior to step (d).

Certain embodiments are directed to a method of producing a multi-use biosensor array assembly. The method comprises forming a plurality of multi-use biosensors on at least one surface of a substrate. Each of the plurality of multi-use biosensors are spatially positioned on the at least one surface of the substrate. At least one of the plurality of multi-use biosensors is formed by any of the methods described immediately herein above.

Certain embodiments are directed to a method for detecting the presence and/or concentration of a target analyte in a fluidic biological sample. The method comprises the steps of: (a) inserting a fluidic biological sample into a blood gas, electrolyte, and/or metabolite instrument containing any of the multi-use biosensors described herein above; and (b) measuring the presence and/or concentration of the target analyte captured by the multi-use biosensor.

Certain embodiments are directed to a method for detecting the presence and/or concentration of a plurality of target analytes in a fluidic biological sample. The method comprises the steps of: (a) inserting a fluidic biological sample into a blood gas, electrolyte, and/or metabolite instrument containing any of the multi-use biosensor array assemblies described herein above; and (b) measuring the presence and/or concentration of each of the plurality of target analytes captured by the individual multi-use biosensors of the array assembly.

In certain embodiments, the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

Thus, in accordance with the presently disclosed inventive concept(s), there have been provided compositions and devices, as well as methods of producing and using same, which fully satisfy the objectives and advantages set forth hereinabove. Although the presently disclosed inventive concept(s) has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed inventive concept(s).

What is claimed is:

1. A multi-use biosensor for detecting the presence and/or concentration of at least one target analyte in a fluidic biological sample, the multi-use biosensor comprising:
   an electrode;
   a modified enzyme dispensed and dried on at least a portion of the electrode, wherein the enzyme has been modified to reduce the solubility thereof through reaction of at least one functional group thereon with a reactant such that the modified enzyme is substantially insoluble in the fluidic biological sample and in calibration reagents utilized with the multi-use biosensor, and wherein the modified enzyme comprises an active site that interacts with the target analyte for detection of the target analyte; and
   a membrane disposed on at least a portion of the modified enzyme, wherein the membrane immobilizes the modified enzyme on the electrode.

2. The multi-use biosensor of claim 1, further defined as a potentiometric analyte biosensor.

3. The multi-use biosensor of claim 1, wherein the at least one functional group on the modified enzyme is selected from the group comprising an aldehyde-, amine-, carbonyl-, carboxyl-, hydroxyl-, ketone-, maleimide-, sulfhydryl-, and thiol-reactive group.

4. The multi-use biosensor of claim 1, wherein the reactant comprises a long chain biotin.

5. The multi-use biosensor of claim 1, wherein the membrane is permeable to the target analyte to be detected but substantially impermeable to the modified enzyme.

6. The multi-use biosensor of claim 1, wherein the membrane is formed of a material selected from the group comprising polyurethane, silicone, poly(vinyl chloride), and combinations thereof.

7. The multi-use biosensor of claim 1, wherein the enzyme is selected from the group comprising urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, and pyruvate dehydrogenase.

8. The multi-use biosensor of claim 1, further defined as a multi-use blood urea nitrogen (BUN) biosensor, and wherein the at least one modified enzyme is a modified urease.

9. The multi-use biosensor of claim 1, wherein the biosensor has at least a 14 day use-life.

10. The multi-use biosensor of claim 1, wherein the modified enzyme is substantially soluble in a buffer that has a lower ionic strength than the fluidic biological sample and the calibration reagents used with the multi-use biosensor.

11. The multi-use biosensor of claim 1, wherein the reactant attached to the enzyme increases the molecular weight and/or changes the isoelectric point of the modified enzyme when compared to the molecular weight and/or isoelectric point of unmodified enzyme.

12. A multi-use biosensor array assembly, comprising:
    a substrate;
    a plurality of multi-use biosensors, wherein each of the plurality of multi-use biosensors are spatially positioned on at least one surface of the substrate, and wherein at least one of the plurality of multi-use biosensors is a multi-use biosensor of claim 1.

13. A method of producing a multi-use biosensor, the method comprising the steps of:
    (a) modifying an enzyme present in a first buffer by reacting at least one functional group on the enzyme with a reactant, thereby producing a modified enzyme that has a reduced solubility when compared to unmodified enzyme such that the modified enzyme is substantially insoluble in the fluidic biological sample and in calibration reagents utilized with the multi-use biosensor, and wherein the modified enzyme comprises an active site that interacts with the target analyte for detection of the target analyte;
    (b) forming a precipitate of modified enzyme;
    (c) redissolving the precipitate of modified enzyme in a second buffer to provide a modified enzyme solution, wherein the second buffer has a lower ionic strength than the first buffer, whereby the modified enzyme is substantially soluble in the second buffer but less soluble or substantially insoluble in the first buffer;
    (d) dispensing a specific amount of the modified enzyme solution on at least a portion of an electrode;
    (e) drying the modified enzyme solution on the electrode; and
    (f) disposing a membrane on at least a portion of the modified enzyme and electrode, wherein the membrane immobilizes the modified enzyme on the electrode.

14. The method of claim 13, wherein the multi-use analyte biosensor is further defined as a potentiometric analyte biosensor.

15. The method of claim 13, wherein at least one of:
    (i) the at least one functional group on the enzyme is selected from the group comprising an aldehyde-, amine-, carbonyl-, carboxyl-, hydroxyl-, ketone-, maleimide-, sulfhydryl-, and thiol-reactive group;
(ii) the reactant comprises a long chain biotin;
(iii) the membrane is permeable to the target analyte to be detected but substantially impermeable to the modified enzyme;
(iv) the membrane is formed of a material selected from the group comprising polyurethane, silicone, poly(vinyl chloride), and combinations thereof;
(v) the enzyme is selected from the group comprising urease, glucose oxidase, glutamate oxidase, lactate oxidase, pyruvate oxidase, sarcosine oxidase, creatinine amidohydrolase, creatine amidinohydrolase, ascorbate oxidase, alcohol oxidase, cholesterol oxidase, choline oxidase, bilirubin oxidase, laccase, tyrosinase, alcohol dehydrogenase, glucose dehydrogenase, glutamate dehydrogenase, lactate dehydrogenase, and pyruvate dehydrogenase; and
(vi) the reactant attached to the enzyme increases the molecular weight and/or changes the isoelectric point of the modified enzyme when compared to the molecular weight and/or isoelectric point of unmodified enzyme.

16. The method of claim 13, wherein the multi-use biosensor is further defined as a multi-use blood urea nitrogen (BUN) biosensor, and wherein the at least one modified enzyme is urease.

17. The method of claim 13, wherein the biosensor so produced has at least a 14 day use-life.

18. The method of claim 13, wherein step (a) reduces the solubility of the modified enzyme to a level whereby the modified enzyme is substantially insoluble in the fluidic biological sample and in calibration reagents utilized with the multi-use biosensor but is substantially soluble in a buffer that has a lower ionic strength than the fluidic biological sample and the calibration reagents.

19. The method of claim 13, further comprising at least one of the steps of:
(g) purifying the enzyme from excipients by buffer exchange into the first buffer prior to step (a); and
(h) measuring an activity of the enzyme prior to step (d).

20. A method of producing a multi-use biosensor array assembly, the method comprising the step of:
forming a plurality of multi-use biosensors on at least one surface of a substrate, wherein each of the plurality of multi-use biosensors are spatially positioned on the at least one surface of the substrate, and wherein at least one of the plurality of multi-use biosensors is formed by the method of claim 13.

21. A method for detecting the presence and/or concentration of a target analyte in a fluidic biological sample, the method comprising the steps of:
(a) inserting a fluidic biological sample into a blood gas, electrolyte, and/or metabolite instrument containing the multi-use biosensor of claim 1; and
(b) measuring the presence and/or concentration of the target analyte captured by the multi-use biosensor.

22. A method for detecting the presence and/or concentration of a plurality of target analytes in a fluidic biological sample, the method comprising the steps of:
(a) inserting a fluidic biological sample into a blood gas, electrolyte, and/or metabolite instrument containing the multi-use biosensor array assembly of claim 12; and
(b) measuring the presence and/or concentration of each of the plurality of target analytes captured by the individual multi-use biosensors of the array assembly.

23. The method of claim 21, wherein the fluidic biological sample is selected from the group comprising blood, plasma, serum, urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

* * * * *